(12) United States Patent
Danieli

(10) Patent No.: US 6,488,948 B1
(45) Date of Patent: Dec. 3, 2002

(54) ANTI-BACTERIAL COMPOSITION AND USE THEREOF FOR SKIN CARE AND FABRIC TREATMENT

(75) Inventor: Jacob Danieli, Buffalo Grove, IL (US)

(73) Assignee: Sintal International, Inc., Miami, FL (US)

( * ) Notice: Subject to any disclaimer, the term of this patent is extended or adjusted under 35 U.S.C. 154(b) by 0 days.

(21) Appl. No.: 09/959,407

(22) Filed: Oct. 26, 2001

Related U.S. Application Data

(60) Provisional application No. 60/132,000, filed on Apr. 30, 1999.

(51) Int. Cl.$^7$ ................................................. A61K 35/78
(52) U.S. Cl. ...................... 424/404; 424/402; 424/736; 514/556; 514/642; 514/724
(58) Field of Search ................................ 424/404, 736, 424/402; 514/556, 642, 724

(56) References Cited

U.S. PATENT DOCUMENTS

| | | | |
|---|---|---|---|
| 4,941,995 A | 7/1990 | Richards | |
| 5,017,617 A | 5/1991 | Kihara et al. | |
| 5,240,322 A | 8/1993 | Haber et al. | |
| 5,420,118 A | 5/1995 | Alban et al. | |
| 5,660,833 A | 8/1997 | Medenica | |
| 6,274,154 B1 | 8/2001 | Chou | |

*Primary Examiner*—Francisco Prats
*Assistant Examiner*—Susan D. Coe
(74) *Attorney, Agent, or Firm*—Venable; Robert J. Frank; Ashley J. Wells

(57) ABSTRACT

This invention relates to a water-based composition having at least one of ant-bacterial or anti-fungal properties and use thereof for skin care and for fabric treatment. The composition is not only effective as an anti-bacterial and/or anti-fungal material when included in a skin care gel or lotion for topical use, such as in a sun screen composition, or in conjunction with sanitary elastic gloves as a coating therein, it is gentle to the user's skin and may include constituents which advantageously indicate its presence. The composition is not only effective as an anti-bacterial and/or anti-fungal material when used as a liquid to treat fabric employed for personal hygiene aids including disposable diapers for children and adults, sanitary napkins, and wipes, it is gentle to the skin and may be formulated to provide odor control. Users include humans and animals.

38 Claims, 2 Drawing Sheets

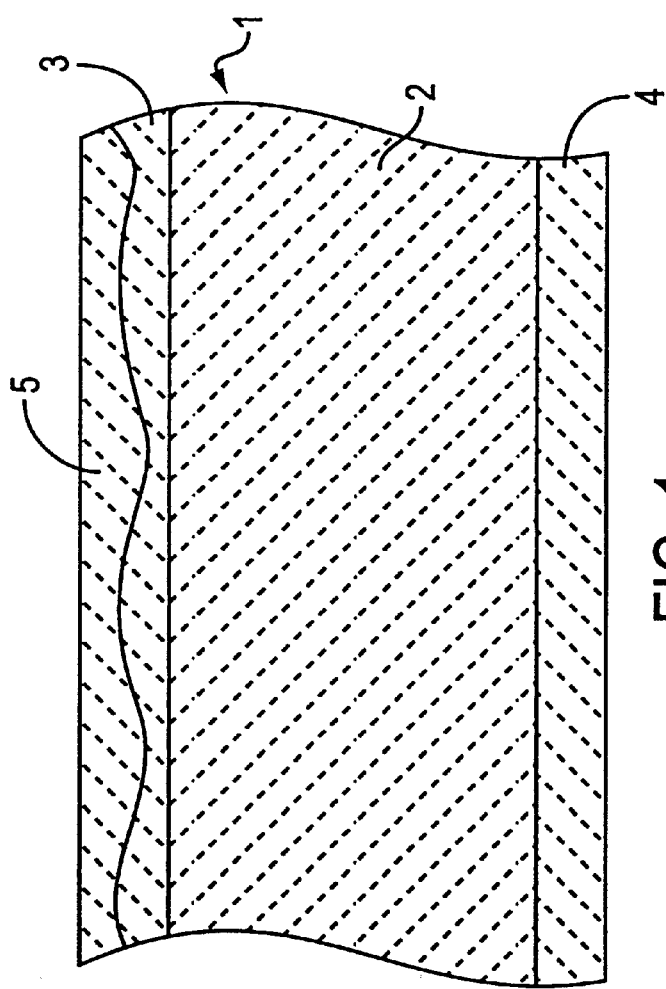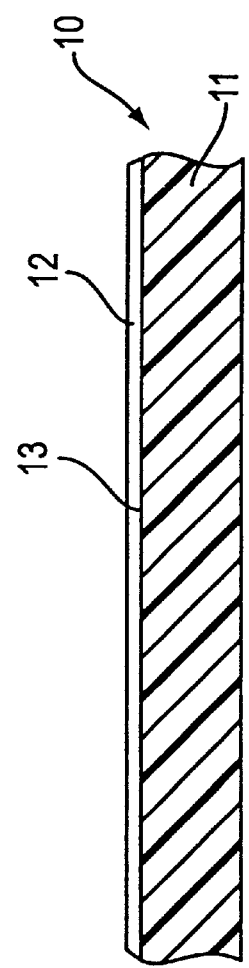

ANTI-BACTERIAL COMPOSITION AND USE THEREOF FOR SKIN CARE AND FABRIC TREATMENT

This application claims the benefit of U.S. Provisional application No. 60/132,000 filed Apr. 30, 1999.

This invention relates to a water-based composition having at least one of anti-bacterial or anti-fungal properties and use thereof for skin care and for fabric treatment. The composition is not only effective as an anti-bacterial and/or anti-fungal material when included in a skin care gel or lotion for topical use, such as in a sun screen composition, or in conjunction with sanitary elastic gloves as a coating therein, it is gentle to the user's skin and may include constituents which advantageously indicate its presence. The composition is not only effective as an anti-bacterial and/or anti-fungal material when used as a liquid to treat fabric employed for personal hygiene aids including disposable diapers for children and adults, sanitary napkins, and wipes, it is gentle to the skin and may be formulated to provide odor control. Users include humans and animals.

Since about May, 1997 the inventor began offering for sale a lotion, which is a water-based composition useful as an antiseptic barrier for pre- and post-milking, and dry period treatment of the teats of milk cows under the trade name tSHIELD™ (Quest Research, Inc.). This composition is formulated as a soothing dip or lotion for topical application or is impregnated in toweling used as a cleansing wipe. The lotion product shields the skin of the cow against bacterial penetration for up to four days and may be marked with a dye to indicate its presence and hence provide an effectiveness indicator.

The composition includes four anti-bacterially-active constituents known to target bacteria commonly found for this application, namely, in % by weight based on the weight of the total composition, 0.30% of a Quaternium 12 (C.T.F.A. name, i.e., a Cosmetic, Toiletries, and Fragrances Association name), such as BORDAC 2250 a disinfectant manufactured by Lonza, Inc.; 2.80% of a Cetrimonium chloride (C.T.F.A. name), which is cetyl trimethyl ammonium chloride, a disinfectant manufactured by Lonza, Inc, under the tradename CARSOQUAT CT-429; 2.80% of a combination of Behentrimonium metholsulfate & stearyl alcohol (C.T.F.A. name), which is a disinfectant manufactured by ISP Corporation; and 0.10% Cetylpyridinium chloride.

The composition additionally includes silicone fluids, i.e., 0.90% of SILICONE 344 and 0.70% of SILICONE 1401 (manufactured by Dow Corning) to improve adherence of the lotion to the cow's teats, as well as other ingredients including emulsifiers, colorants, such as about 0.0023% by weight of FD&C Red, fragrances, and diluents, such as from about 85 to about 90% deionized water.

In about May, 1998, the inventor began offering for sale a water-based gel composition useful as an anti-bacterial hand wash for humans, particularly in medical hygiene applications, under the trade name QUATRO-DERM™ (Quest Research, Inc.). This composition includes four active constituents, hence the name "quatro", namely, in % by weight based on the weight of the total composition, 0.1% of a Quaternium 12 (C.T.F.A. name), such as BORDAC 2250 a disinfectant manufactured by Lonza, Inc.; 0.5% of Didecyl-imethyl ammonium chloride; 1.0% of a Cetrimonium Chloride (C.T.F.A. name), which is cetyl trimethyl ammonium chloride, a disinfectant manufactured by Lonza, Inc. under the tradename CARSOQUAT CT-429; and 0.04% of CHG 20% (a chlorohexidine gluconate manufactured by Degussa AG).

The composition additionally includes various other constituents, such as 1.25% of METHOCEL 40-101 (manufactured by Dow Chemical Corporation) as a thickening agent to provide a viscosity of about 4000 centipoise to the composition, and 0.5% GERMABEN II (manufactured by ISP Corporation) as a formaldehyde donor for the composition.

This composition was not as gentle to the user's skin as was desired, suffered from color instability, and, in any event, was not free of formaldehyde due to the presence of GERMABEN II.

It is an object of the present invention to provide an anti-bacterial composition, which is gentle, which can be used repetitively, and yet which is ant-bacterially effective for humans and animals.

It is another object of the present invention to provide an anti-bacterial composition, which is gentle, which can be used repetitively, and yet which is ant-bacterially effective for humans and animals, and which leaves no visible residue yet has a sustained functional activity.

It is a further object of the present invention to provide an anti-fungal composition, which is gentle, which can be used repetitively, and yet which is effective as an anti-fungal material for humans and animals.

It is another object of the present invention to provide a fabric hygiene article, such as a disposable diaper (child and adult), a feminine hygiene pad, and a wipe for men and women but having particular utility for women for use in the groin, rectum, inner ears, eyelids, and for makeup removal which also treats the skin, containing the anti-bacterial and/or antifungal composition of the present invention.

It is yet another object of the present invention to provide a sanitary elastic glove having a coating provided on at least the inner surface thereof comprising an anti-bacterial and/or anti-fungal composition of the present invention.

These and other objects are accomplished by the present invention which provides a composition which is a gel or lotion and which has at least one of ant-bacterial or anti-fungal properties, comprising from about 85 to about 90% by weight of pure water, such as deionized water, from about 0.80 to about 1.3% by weight of Cetrimonium chloride; and from about 0.07 to about 0.08% by weight of at least one substance selected from the group consisting of Benzalkonium chloride and Grapefruit seed extract; from about 0.15 to about 0.35% by weight of Didecyl-dimethyl ammonium chloride; and from about 0.08% to about 1.55% of Quaternium 22.

The gel or lotion composition is a non-toxic, nonflammable, nondrying, non-irritating cleanser. It is advantageously alcohol-free, pH balanced, and does not leave any residue on body parts such as the breasts of nursing mothers or in the mother's milk.

The compositions according to the invention contain no toxic metals, such as arsenic, and no formaldehyde, yet have a very long shelf life. The compositions are gentle enough for any skin type including, but not limited to, lips, breasts, groin, rectal, and eye areas, and may be used repetitively with no adverse effects.

The present invention additionally provides a fabric hygiene article selected from the group consisting of a disposable diaper, a feminine hygiene pad, and a wipe, comprising a fabric assembly; and a water-based composition comprised of from about 85 to about 90% by weight of water; from about 2.20 to about 3.00% by weight of a mixture of Behentrimonium methosulfate and stearyl alcohol; from about 0.15 to about 0.33% by weight of Quaternium 12; from about from about 0.80 to about 3.00% by weight of Cetrimonium chloride; and from about 0.08% to about 1.55% of Cetylpyridinium chloride present in an amount which is at least effective to provide anti-bacterial and/or anti-fingal properties to the surface of the fabric assembly which contacts the user. The amount of composition used may range up to an amount which does not substantially prevent moisture uptake by the fabric assembly. The wipe is preferably completely saturated by the water-based composition and is made of a non-woven fabric composed of a material such as a natural material, for example, a cotton pulp, or a synthetic material such as polyester fibers.

The present invention further provides a sanitary glove, comprising a glove comprised of an elastic material; and a coating provided on at least a part of the inner surface of the glove and being comprised of a water-based composition having at least one of anti-bacterial or anti-fungal properties and comprising from about 85 to about 90% by weight of water; from about 2.20 to about 3.00% by weight of a mixture of Behentrimonium methosulfate and stearyl alcohol; from about 0.15 to about 0.33% by weight of Quaternium 12; from about 0.80 to about 3.00% by weight of Cetrimonium chloride; and from about 0.08% to about 1.55% of Cetylpyridinium chloride.

The composition for skin care of the present invention includes four ant-bacterially active constituents, namely, from about 0.80 to about 1.30%, preferably about 1.20%, by weight of Cetrimonium chloride and from about 0.07 to about 0.08%, preferably about 0.08%, by weight of at least one substance selected from the group consisting of Benzalkonium chloride and Grapefruit seed extract; from about 0.15 to about 0.35%, preferably about 0.30, by weight of Didecyl-imethyl ammonium chloride; and from about 0.08% to about 1.55%, preferably about 0.1%, of Quaternium 22 (C.T.F.A. name), such as those manufactured by manufactured by Lonza, Inc. as anti-bacterially effective constituents. These materials are additionally effective as anti-fungal materials. When one or more of these four active constituents are used in small concentrations, they then function more as a preservative.

The composition of the present invention may additionally include thickening agents, such as from about 0.09 to about 1.20%, preferably about 1.00%, by weight of NATRASOOL HHR 250 manufactured by Aqualon Corporation or METHOCEL 40-101 manufactured by Dow.

The composition additionally may includes moisturizers, such as from about 0.09 to about 0.12%, preferably about 0.10%, by weight of aloe vera extract. Lanolin or glycerine may be included, and additional materials such as Vitamin E and citric acid may be added.

The composition may additionally include an orgonolepticically effective constituent for odor control, namely, from about 1.00 to about 2.50%, preferably about 2.50%, by weight of a sodium salt of an organic sesquicarbonate, such as those manufactured by Dow Chemical.

The anti-bacterial composition for sanitary elastic glove application of the present invention includes four anti-bacterially active constituents, namely, from about 0.15 to about 0.33%, preferably about 0.30%, by weight of Quaternium 12 (C.T.F.A. name) such as that manufactured by Lonza, Inc.; from about 0.80 to about 3.00%, preferably 2.80%, by weight of Cetrimonium chloride; from about 2.20 to about 3.00%, preferably about 2.80%, by weight of a mixture of Behentrimonium methosulfate and stearyl alcohol (C.T.F.A. name); and from about 0.08 to about 1.55%, preferably 0.10% by weight of Cetylpyridinium chloride (C.T.F.A. name), such as those manufactured by Croda, as anti-bacterially effective constituents. These materials are additionally effective as anti-fingal materials.

The composition of the present invention additionally includes thickening agents, such as from about 0.80 to about 1.20%, preferably about 0.90%, by weight of CYCLOMETHICONE manufactured by Dow Chemical, and from about 0.05 to about 0.90%, preferably about 0.07%, by weight of CYCLOMETHICONE DIMETHICONOL manufactured by Dow Chemical.

The composition additionally includes moisturizers, such as from about 0.09 to about 0.12%, preferably about 0.10%, by weight of aloe vera extract, and Vitamin E and glycerin.

The composition may additionally include an orgonolepticically effective constituent for odor control, namely, from about 1.00 to about 2.50%, preferably about 2.50%, by weight of a sodium salt of an organic sesquicarbonate.

The composition may additionally include an indicator for activity which advises a human user or observer of the presence or absence of the composition either by color, or absence thereof, or by fragrance or absence thereof. For example, a dye may be employed such as, by way of example but not limitation, FD&C Red #28 or Red Fluorescent #40. The dye material, moreover, may have any suitable color and may change color depending on the pH of the skin of the recipient. Any suitable water-soluble fragrance may be used, such as those manufactured by ARILYESSENCE. For example, cherry fragrance may be included.

Further advantages and features will become apparent from the detailed description below taken with the drawings in which:

FIG. 1 illustrates in cross-section a treated fabric assembly, such as commonly employed in a sanitary napkin or disposable diaper, showing that the ant-bacterial and/or anti-fungal composition of the present invention is impregnated into at least the surface of the fabric assembly which contacts the user's skin;

FIG. 2 illustrates in cross-section a portion of a sanitary elastic glove provided on its inner surface with a coating composed of the anti-bacterial and/or anti-fungal composition of the present invention.

Figure 3:
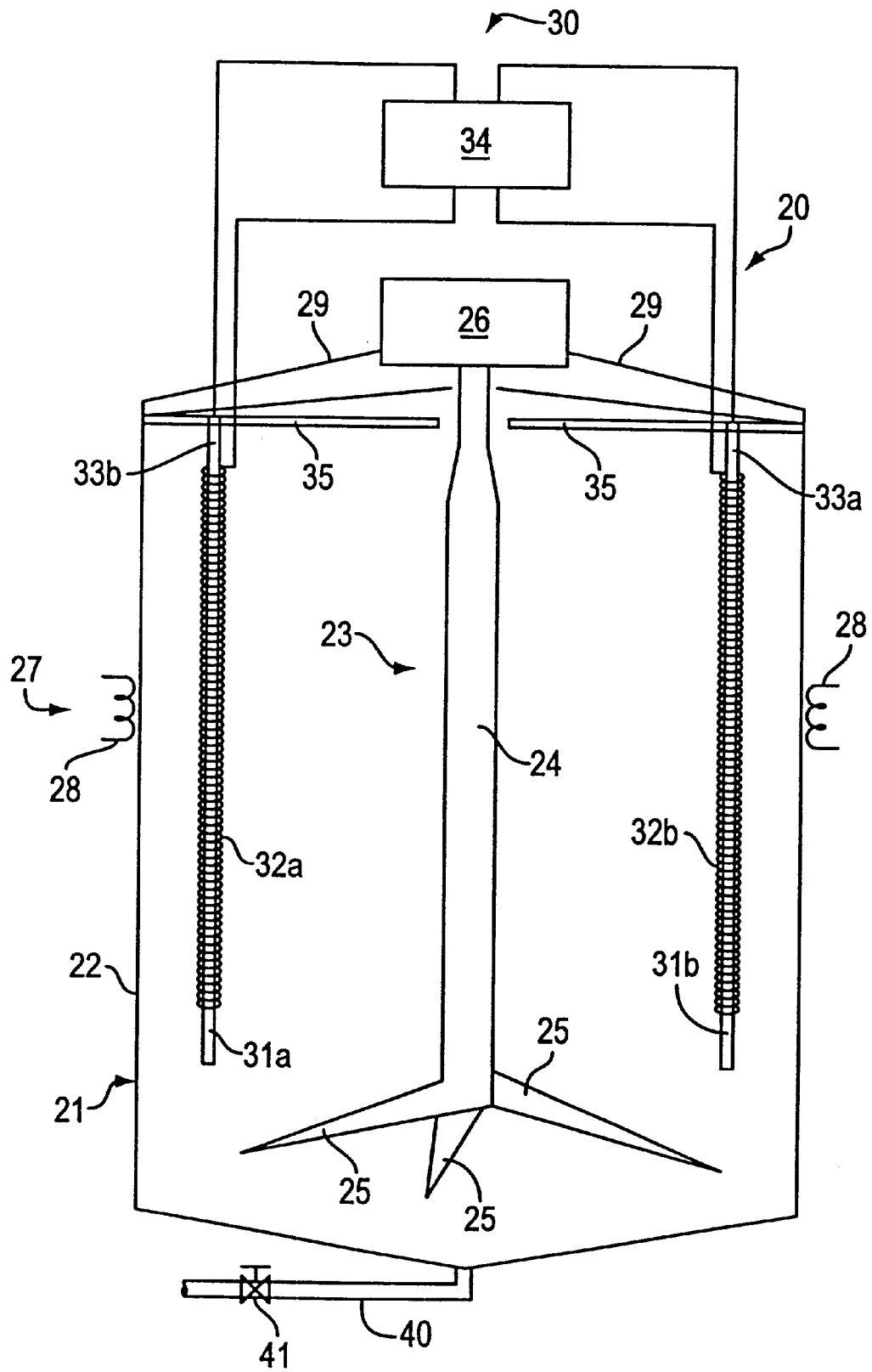
FIG. 3 schematically illustrates an apparatus for mixing and magnetically treating a composition according to the invention.

FIG. 1 shows a cross-section of a treated fabric assembly 1 having an inner padding 2 and outer fabric cover layers 3, 4, such as commonly employed in a sanitary napkin or in a disposable diaper, with the anti-bacterial and/or anti-fungal composition of the present invention impregnated into at least a surface area 5 of the outer cover layer 3 which contacts the user's skin.

FIG. 2 shows in cross-section a portion of an elastic glove 10 including an elastic layer 11 composed of, for example latex or vinyl, and a coating 12 composed of the anti-bacterial and/or anti-fungal composition of the present invention applied as a coating onto inner surface 13 of the latex glove 10.

FIG. 3 schematically illustrates an apparatus 20 for mixing and magnetically treating a composition according to the invention. The apparatus includes a mixing vessel 21 including a tank 22, stirring means 23 shown as a shaft 24 provided with stirring blades 25 powered by a motor 26, heating means 27 shown as resistance heater 28 (not to scale), and lids 29 for retaining heat within the vessel 21. A magnetic field generation means shown generally at 30 is positioned in a manner effective to magnetically influence the composition within the tank. In the schematic illustration of FIG. 3, the magnetic field generation means 30 includes at least two electrodes 31 (anode 31a and cathode 31b) provided with wound coils of wire 32a, 32b respectively surrounding conductive metal rods 33a, 33b, and at least one D.C. power source 34 sufficient to provide a current at the at least two electrodes 31a, 31b ranging from about 20 up to but less than about 40 amperes. The at least two electrodes 31 are mounted on a bridge 35 which extends the width of the tank 22 but which is electrically insulated from tank 22 which may be made of stainless steel. The tank 22 is provided with a drain line 40 and valve 41.

The apparatus of FIG. 3 may be employed to practice a method of manufacturing a composition according to the invention, which method includes, in the order recited, providing the mixing vessel 21 including the tank 22, stirring means 23 positioned within the tank 22, and a magnetic field generation means 30 positioned in a manner effective to magnetically influence the composition within the tank 22. The mixing vessel 21 is filled with about one half of the water and the water is heated to a temperature of about 50° C. The at least four active ingredients of the composition of according to the invention are added to the water in the mixing vessel 21, and are stirred slowly and at low shear to provide a pre-mix. The pre-mix is treated in a magnetic field having a field strength and for a time effective to increase specific gravity of the pre-mix to a specific gravity ranging from 1.015 to 1.018. The remainder of the water is added to provide a treated mixture.

The water is advantageously allowed to relax, i.e., settle, prior to heating. The at least four active ingredients are preferably added to the water in the mixing vessel 21 slowly, sequentially, and with the stirring means 23 operating at low shear.

The method may additionally include adding at least one additional constituent to the treated mixture slowly and with mixing at low shear. The at least one additional constituent is advantageously selected from the group consisting of a thickening agent, a moisturizer, a surfactant, an organoleptically effective ingredient for odor control, a dye, and a fragrance, examples of which are discussed in the following. When at least two additional constituents are added to the treated mixture, to the method advantageously additionally includes mixing the at least two additional constituents together in a separate vessel (not shown) prior to adding same to the treated mixture in vessel 21.

The pre-mix is treated in a magnetic field for a time ranging from about 1 to about 60 minutes, preferably, for a time ranging from about 20 to about 40 minutes.

Pilot Plant Apparatus

The mixing vessel employed was cylindrical as illustrated in FIG. 3 and had a diameter of about six and one half feet and a depth of about four feet. Batches of about 250 gallons were made and each batch filled the mixing vessel to a depth of about three feet. Two electrodes for generating a magnetic field were provided, i.e., an anode and a cathode, and were separated from one another by a distance of about six feet. The stirring blades extended about six feet taken as a whole, were positioned beneath the lower ends of the two electrodes, and were powered by a one half horsepower, variable speed motor.

The anode and cathode were each constructed of about 25 foot lengths of current-carrying copper wire which had a thickness of about that of telephone wire and which was wound around a three foot length of steel rod having a one and one quater inch diameter. The wire was wound in the middle portion of the respective steel rods. No wire was wound on the ends of the steel rods so that about six inches of rod remained at each respective end thereof. The wire was coiled into a series of turns which were positioned as close together as possible.

The magnetic field generation means was advantageously configured to provide a current at the coils of about 30 amps for time period of about 20 minutes, with a D.C. voltage applied of about 24 volts. These parameters are provided by way of example, but not limitation. As one of skill in the magnetic art would recognize, the parameters which define the electric field, including the length of the electrodes, the distance between them, and the D.C. voltage applied to them, may be varied over a wide range. Similarly, the parameters which define the magnetic field, including the number of turns, the cross-sectional area of the coils, and the current at the coils, may be varied over a wide range.

The color and the specific gravity of the mixture varied during magnetic treatment and were used to monitor progress. The color of the mixture starts out as water white and turns a light yellow during magnetic treatment indicating that some type of change is occurring, such as perhaps formation of a complex or coordination compound between one or more of the four active ingredients. Current below about 20 amps was found to require too much time for the desired changes in color and specific gravity to occur. Current of 40 amps or more was found to undesirably turn the composition a dark yellow-brown color. The specific gravity of the compositions being magnetically treated gradually increased to a range of from 1.015 to 1.018.

In the pilot plant apparatus employed, the magnetic field generation means produced a large field parallel to the axis of the electrodes (in the z-direction). Between these magnetic field generation electrodes (anode and cathode), the fields from individual coils added together to form a very strong field along the center line between the anode and the cathode. Components of the magnetic field in other directions were cancelled by opposing fields from neighboring coils. Outside of the magnetic field generation means, the magnetic field was very weak due to the cancellation effect. For magnetic field generation electrodes that are long in comparison to their diameter, the field is very close to zero.

While the magnetic field was not measured, the magnitude of the magnetic field was calculated using Ampere's law. Ampere's law relates to the circulation of B around a closed loop to the current flux through the loop×$\mu o$ (Formula 1). This gives the magnetic field along the center line between the electrodes. It is noted that since the magnitude of the current changes with time, so also does Bo, i.e., for a sinusoidally varying current, N/L is the amplitude (maximum value) of the field. Thus, one can also refer to the value of | Bo | called, the root-mean-square (RMS) value, and BRMS=|Bo|/sqrt (Formula 2).

The time-variation of the magnetic field also shows BRMS. However, this doesn't tell you what the magnetic field outside the electrodes is. To calculate this you need to use the Biot-Savart law. From symmetry, along the z-axis all the components of the field due to a current loop cancel, except the component in the z-direction. So $B$ (Formula 3) at a position z along the axis of the electrode(s) is given by where R=radius of the loop. This Formula 3 shows B as a function of z when z; R. Note that B decreases rapidly as z increases.

EXAMPLE 1

Glove Coating Composition (QUATROGLOVE) and Method

A composition suitable for dip coating the interior of an elastic glove was prepared and included the following constituents in amounts by weight as stated.

0.5% of N-alkyl-dimethylbenzyl-ammonium chloride (for example, BARQUAT MB-50, by Lonza, Inc. or Pacific Coast Chemicals);

1.0% of Cetramonium Chloride (for example, CARSO-QUAT CT429, Cetyl-trimethylammonium chloride, by Lonza, Inc. or Pacific Coast Chemicals);

1.0% of OCTOXYNOL-9;

0.2% of Quaternium 22;

2.4% of Chlorohexadine gluconate (CHG, 4%);

0.1% of cherry fragrance;

30.0% of Dimethicone (a silicone fluid);

2.0% of Incroquat Behenyl (tms); and 62.79% of water (deionized water or distilled water is used).

About half of the water was filled into a first mixing vessel, which corresponded to the pilot plant apparatus schematically illustrated in FIG. 3, was allowed to relax, and was heated to about 50° C. The N-alkyl-dimethylbenzyl-ammonium chloride, Cetramonium Chloride, OCTOXYNOL-9, Quaterniun 22, and Chlorohexadine gluconate were added to the heated water slowly and sequentially, and were stirring slowly and at low shear to provide a first mixture. The first mixture was treated in a magnetic field having a field strength and for a time effective to increase specific gravity of the first mixture to a specific gravity ranging from 1.015 to 1.018, i.e., about 20 to 30 minutes.

The color of the first mixture was seen to change from a clear water-white to a light yellow color which the inventor considers may be due to formation of a complex having extended conjugation and hence the color change. Moreover, treatment in a magnetic field took place at a current at the magnetic coils of about 30 amps with about 24 volts applied. If the current was lowered to about 20 amps, the treatment required an impractical, extended amount of time to achieve the desired specific gravity range. If the current was increased to 40 amps, the mixture turned an aesthetically unpleasant dark yellow-brown color which, as a practical matter, would not be useful for this type of composition and which may be due, at least in part, to undesirable electrolysis of the constituents.

The remaining half of the water was filled into a second mixing vessel and heated to a temperature of about 50° C. The Cherry Fragrance, Dimethicone (a silicone fluid), and Incroquat Behenyl (tms) were added to the water in the second mixing vessel and were stirred to obtain a second mixture having a specific gravity of 0.87. This second mixing vessel was not provided with a magnetic treatment means.

The second mixture was then slowly added to the first mixture in the first mixing vessel with stirring at low shear to provide a composition suitable for spray coating the interior of an elastic glove. The pH of the composition ranged between 5.5 to 7.0. The specific gravity of the composition ranged between 0.85 to 0.89 with respect to water.

A latex composition was coated onto a mold maintained at about 50° C. to form a green latex glove. The green latex glove while still on the mold was dipped into the composition according to the invention to form a coating thereon, and was dried in a hot air tunnel maintained at a temperature ranging from about 110 to 120° C. The glove was removed from the mold and turned inside out so that the coating of the inventive composition was present on the inside of the glove.

EXAMPLE 2

Glove coating Composition (QUATROGLOVE)

A liquid composition having a viscosity of 800 cps was prepared and included the following four active constituents as percent by weight:

0.13% of Quaternium 12 (useful range 0.08–0.13%);

2.8% of Cetrimonium chloride (useful range 0.80–3.00%);

2.8% of a mixture of Behentimonium methosulfate and Stearyl alcohol (useful range 2.20–3.00%); and 0.1% of Cetylpyridinium chloride (useful range 0.08–1.55%). These were mixed in an apparatus and treated with a magnetic field as described in Example 1.

The composition additionally included the following constituents which were mixed in a second vessel, heated, and subsequently added to the mixed and magnetically treated active ingredients in the apparatus mentioned above:

(1) a thickening agent comprised of.
  30.00% of cyclomethicone (useful range 27.20–33.80%); and
  0.70% of cyclomethicone dimethiconol (useful range 0.05–0.90%);

(2) a moisturizer comprised of 0.1% of aloe vera extract (useful range 0.09–0.12%);

(3) a constituent which serves to remove objectionable odors which is 1.0% of at least one sodium salt of an organic sesquicarbonate (useful range 1.00–2.50%); and (4) an indicator for presence of the composition which is a dye and which is 0.0023% of FC&C red #28 (useful range 0.0021–0.0024%); and/or which is a water-soluble fragrance and which is 0.01% of a cherry fragrance (useful range 0.01–0.012%).

EXAMPLE 3

Liquid/Gel Composition (QUATROGUARD)

A liquid composition having a specific gravity of 1.01 was prepared and included water and the following four active constituents as percent by weight:

1.2% of Cetrimonium chloride (useful range 0.80–1.30%);

0.3% of Didecyl-dimethyl ammonium chloride (useful range 0.15–0.35%);

0.1% of Quaternium 22 (useful range 0.08–1.55%); and 0.08% of Benzalkonium chloride (useful range 0.07–0.13%). These were mixed in an apparatus and treated for 20 minutes with a magnetic field as described in Example 1. This mixture was then allowed to stand for 30 minutes. Stirring was resumed at low shear and additional constituents were added as follows:

(1) a thickening agent which is 1.0% of Natrosool HHR 250 (useful range 0.002–1.50%); and (2) a moisturizer which is 0.1% of aloe vera extract (useful range 0.09–0.12%).

The composition additionally included the following constituents which were mixed with water in a second vessel, heated, and subsequently added to the mixed and magnetically treated active ingredients in the apparatus mentioned above:

(1) a constituent which serves to remove objectionable odors which is 2.50% of at least one sodium salt of an organic sesquicarbonate (useful range 1.00–2.50%); and (2) at least one water-soluble fragrance and which is 0.01% of a cherry fragrance (useful range 0.01–0.012%).

This composition can be prepared as a liquid or as a gel by varying the amount of constituents, particularly the thickener as one skilled in the art would understand. This composition or any composition according to the invention can be prepared without the magnetic treatment and be useful for the stated purposes. Magnetic treatment of the active ingredients, however, significantly lengthens the period of time the composition provides functional activity, e.g., anti-bacterial or anti-fungal properties, to the applied area of the recipient, human or animal. An additional advantage is that the magnetically treated composition leaves no visible residue on the applied area of the recipient, human or animal.

It is understood that various other modifications will be apparent to and can be readily made by those skilled in the art without departing from the scope and spirit of the present invention. Accordingly, it is not intended that the scope of the claims appended hereto be limited to the description set forth above but rather that the claims be construed as encompassing all of the features of patentable novelty which reside in the present invention, including all features which would be treated as equivalents thereof by those skilled in the art to which the invention pertains.

What is claimed is:

1. A water-based composition having at least one of anti-bacterial or anti-fungal properties, which properties are stabilized by treatment in a magnetic field under conditions effective to form a complex, comprising:
    from about 85 to about 90% by weight of water; and
    at least four active ingredients including:
        from about 0.80 to about 1.30% by weight of Cetrimonium chloride;
        from about 0.07 to about 0.08% by weight of at least one substance selected from the group consisting of Benzalkonium chloride and Grapefruit seed extract;
        from about 0.15 to about 0.35% by weight of Didecyldimethyl ammonium chloride; and
        from about 0.08% to about 1.55% of Quaternium 22,
    wherein the at least four active ingredients and at least a part of the water are combined and subjected to a magnetic field under conditions effective to form a complex so that the at least one of anti-bacterial or anti-fungal properties are stabilized, and
    wherein the remainder of the water is added to the stabilized composition.

2. The water-based composition according to claim 1, further comprising a thickening agent.

3. The water-based composition according to claim 2, wherein the thickening agent is at least one substance selected from the group consisting of NATRASOOL HHR 250 and METHOCEL 40-101, and is present in an amount ranging from about 0.09 to about 1.20 % by weight.

4. The water-based composition according to claim 1, further comprising a moisturizer.

5. The water-based composition according to claim 4, wherein the moisturizer is at least one substance selected from the group consisting of aloe vera extract, Vitamin E, citric acid, and glycerin, and is present in an amount ranging from about 0.09 to about 0.12% by weight.

6. The water-based composition according to claim 1, further comprising an orgonolepticically effective constituent for odor control.

7. The water-based composition according to claim 6, wherein the organoleptically effective constituent is at least one sodium salt of an organic sesquicarbonate and is present in an amount ranging from about 1.00 to about 2.50% by weight.

8. The water-based composition according to claim 1, further comprising at least one of a dye or a fragrance.

9. A fabric hygiene article selected from the group consisting of a diaper, a sanitary napkin and a wipe, comprising:
    a fabric assembly; and
    a water-based composition having at least one of anti-bacterial or anti-fingal properties, which properties are stabilized by treatment in a magnetic field, and being comprised of:
        from about 85 to about 90% by weight of water; and
        at least four active ingredients including:
            from about 2.20 to about 3.00% by weight of a mixture containing Behentrimonium methosulfate and stearyl alcohol;
            from about 0.15 to about 0.33% by weight of Quaternium 12;
            from about 0.80 to about 3.00% by weight of Cetrimonium chloride; and
            from about 0.08% to about 1.55% of Cetylpyridinium chlorides,
    wherein the at least four active ingredients and at least a part of the water are combined and subjected to a magnetic field under conditions effective to form a complex so that the at least one of anti-bacterial or anti-fungal properties are stabilized, and
    wherein the remainder of the water is added to the stabilized composition.

10. The fabric hygiene article according to claim 9, further comprising a thickening agent.

11. The fabric hygiene article according to claim 10, wherein the thickening agent comprises:
    from about 0.80 to about 1.20% by weight of Cyclomethicone; and
    from about 0.05 to about 0.90% by weight of Cyclomethicone dimethiconol.

12. The fabric hygiene article according to claim 9, further comprising a moisturizer.

13. The fabric hygiene article according to claim 12, wherein the moisturizer is at least one substance selected from the group consisting of aloe vera extract, Vitamin E, glycerin and citric acid, and is present in an amount ranging from about 0.09 to about 0.12% by weight.

14. The fabric hygiene article according to claim 9, further comprising an orgonolepticically effective constituent for odor control.

15. The fabric hygiene article according to claim 14, wherein the organoleptically effective constituent is at least one a sodium salt of an organic sesquicarbonate and is present in an amount ranging from about 1.00 to about 2.50% by weight.

16. The fabric hygiene article according to claim 9, further comprising at least one of from about 0.0021 to about 0.0024% by weight of a dye or a fragrance.

17. A sanitary glove, comprising:
    a glove comprised of an elastic material; and
    a coating provided on at least a part of the inner surface of the glove and being comprised of a water-based composition having at least one of anti-bacterial or anti-fungal properties, which properties are stabilized by treatment in a magnetic field under conditions effective to form a complex, and comprising:
        from about 85 to about 90% by weight of water; and
        at least four active ingredients including:
            from about 2.20 to about 3.00% by weight of a mixture containing Behentrimonium methosulfate and stearyl alcohol;

from about 0.15 to about 0.33% by weight of Quaternium 12;

from about 0.80 to about 3.00% by weight of Cetrimonium chloride; and from about 0.08% to about 1.55% of Cetylpyridinium Chloride;

wherein the at least four active ingredients and at least a part of the water are combined and subjected to a magnetic field under conditions effective to form a complex so that the at least one of anti-bacterial or anti-fingal properties are stabilized, and wherein the remainder of the water is added to the stabilized composition.

18. The sanitary glove according to claim 17, wherein the water-based composition further comprises a thickening agent.

19. The sanitary glove according to claim 18, wherein the thickening agent comprises:

from about 0.80 to about 1.20% by weight of Cyclomethicone; and from about 0.05 to about 0.90% by weight of Cyclomethicone dimethiconol.

20. The sanitary glove according to claim 17, wherein the water-based composition further comprises a moisturizer.

21. The sanitary glove according to claim 20, wherein the moisturizer is at least one substance selected from the group consisting of aloe vera extract, citric acid, glycerin and Vitamin E, and is present in an amount ranging from about 0.09 to about 0.12% by weight.

22. The sanitary glove according to claim 17, wherein the water-based composition further comprises an orgonoleptically effective constituent for odor control.

23. The sanitary glove according to claim 22, wherein the organoleptically effective constituent is at least one a sodium salt of an organic sesquicarbonate and is present in an amount ranging from about 1.00 to about 2.50% by weight.

24. The sanitary glove according to claim 17, wherein the water-based composition further comprises at least one of from about 0.0021 to about 0.0024% by weight of a dye or a fragrance.

25. The sanitary glove according to claim 17, wherein the elastic material is one of latex or vinyl.

26. A method of manufacturing a water-based composition according to claim 1, comprising, in the order recited:

providing a mixing vessel including a tank, stirring means positioned within the tank, and a magnetic field generation means positioned in a manner effective to magnetically influence the composition within the tank;

filling the mixing vessel with at least some of the water;

heating the water to a temperature of about 50° C.;

adding the at least four active ingredients to the water in the mixing vessel;

stirring slowly and at low shear to provide a pre-mix;

treating the pre-mix in a magnetic field having a field strength and for a time effective to form a complex; and adding the remainder of the water to provide a treated mixture.

27. The method according to claim 26, wherein the magnetic field generation means comprises at least two electrodes provided with wound coils of wire, and at least one D.C. power source sufficient to provide a current at the at least two electrodes ranging from about 20 up to but less than about 40 amperes.

28. The method according to claim 26, further comprising allowing the water to settle prior to heating same; and adding the at least four active ingredients to the water in the mixing vessel slowly, sequentially, and at low shear.

29. The method according to claim 26, further comprising adding at least one additional constituent to the treated mixture slowly and with mixing at low shear.

30. The method according to claim 29, wherein the at least one additional constituent is selected from the group consisting of a thickening agent, a moisturizer, a surfactant, an organoleptically effective ingredient for odor control, a dye, and a fragrance.

31. The method according to claim 29, wherein at least two additional constituents are added to the treated mixture and the method further comprises mixing the at least two additional constituents together in a separate vessel prior to adding same to the treated mixture.

32. The method according to claim 26, wherein the pre-mix is treated in a magnetic field for a time ranging from about 1 to about 60 minutes.

33. The method according to claim 32, wherein the pre-mix is treated in a magnetic field for a time ranging from about 20 to about 40 minutes.

34. The method according to claim 26, wherein the premix is treated in a magnetic field having a field strength and for a time effective to increase specific gravity of the pre-mix to a specific gravity ranging from 1.015 to 1.018.

35. A method of manufacturing a water-based composition according to claim 9, comprising, in the order recited:

providing a mixing vessel including a tank, stirring means positioned within the tank, and a magnetic field generation means positioned in a manner effective to magnetically influence the composition within the tank;

filling the mixing vessel with at least some of the water;

heating the water to a temperature of about 50° C.;

adding the at least four active ingredients to the water in the mixing vessel;

stirring slowly and at low shear to provide a pre-mix;

treating the pre-mix in a magnetic field having a field strength and for a time effective to form a complex; and adding the remainder of the water to provide a treated mixture.

36. A method of manufacturing a water-based composition according to claim 17, comprising, in the order recited:

providing a mixing vessel including a tank, stirring means positioned within the tank, and a magnetic field generation means positioned in a manner effective to magnetically influence the composition within the tank;

filling the mixing vessel with at least some of the water;

heating the water to a temperature of about 50° C.;

adding the at least four active ingredients to the water in the mixing vessel;

stirring slowly and at low shear to provide a pre-mix;

treating the pre-mix in a magnetic field having a field strength and for a time effective to form a complex; and adding the remainder of the water to provide a treated mixture.

37. A water-based fabric impregnating composition having at least one of anti-bacterial or anti-fungal properties, which properties are stabilized by treatment in a magnetic field, and comprising:

from about 85 to about 90% by weight of water; and at least four active ingredients including:

from about 2.20 to about 3.00% by weight of a mixture containing Behentrimonium methosulfate and stearyl alcohol;

from about 0.15 to about 0.33% by weight of Quaternium 12;

from about 0.80 to about 3.00% by weight of Cetrimonium chloride; and from about 0.08% to about 1.55% of Cetylpyridinium chloride, wherein the at least four active ingredients and at least a part of the water are combined and subjected to a magnetic field under conditions effective to form a complex so that the at least one of anti-bacterial or anti-fungal properties are stabilized, and wherein the remainder of the water is added to the stabilized composition.

38. A water-based coating composition having at least one of ant-bacterial or anti-fungal properties, which properties are stabilized by treatment in a magnetic field under conditions effective to form a complex, and comprising:

from about 85 to about 90% by weight of water; and at least four active ingredients including:

from about 2.20 to about 3.00% by weight of a mixture containing Behentrimonium methosulfate and stearyl alcohol;

from about 0.15 to about 0.33% by weight of Quaternium 12;

from about 0.80 to about 3.00% by weight of Cetrimonium chloride; and from about 0.08% to about 1.55% of Cetylpyridinium Chloride, wherein the at least four active ingredients and at least a part of the water are combined and subjected to a magnetic field under conditions effective to form a complex so that the at least one of anti-bacterial or anti-fungal properties are stabilized, and wherein the remainder of the water is added to the stabilized composition.

* * * * *

UNITED STATES PATENT AND TRADEMARK OFFICE
CERTIFICATE OF CORRECTION

PATENT NO.   : 6,488,948 B1
DATED        : December 3, 2002
INVENTOR(S)  : Jacob Danieli It is certified that error appears in the above-identified patent and that said Letters Patent is hereby corrected as shown below:

<u>Title page,</u>
After item [22], insert:
-- [22] PCT Filed:       April 28, 2000
[86] PCT No.:            PCT/US00/11425
[87] PCT Pub. No.:       WO 00/65911
     PCT Pub. Date:      November 9, 2000 --

Signed and Sealed this

Second Day of December, 2003

JAMES E. ROGAN
*Director of the United States Patent and Trademark Office*